US012558422B2

(12) United States Patent
Maeder et al.

(10) Patent No.: US 12,558,422 B2
(45) Date of Patent: \*Feb. 24, 2026

(54) IMMUNOGLOBULIN PREPARATION AND STORAGE SYSTEM FOR AN IMMUNOGLOBULIN PREPARATION

(71) Applicant: CSL Behring AG, Bern (CH)

(72) Inventors: Werner Maeder, Oftringen (CH); Reinhard Franz Bolli, Gümligen (CH); Peter Lerch, Bern (CH); Renzo Pedrussio, Koeniz (CH); Liane Hoefferer, Ostermundigen (CH)

(73) Assignee: CSL Behring AG, Bern (CH)

( \* ) Notice: Subject to any disclaimer, the term of this patent is extended or adjusted under 35 U.S.C. 154(b) by 582 days.

This patent is subject to a terminal disclaimer.

(21) Appl. No.: 17/864,622

(22) Filed: Jul. 14, 2022

(65) Prior Publication Data

US 2023/0083398 A1     Mar. 16, 2023

Related U.S. Application Data

(60) Continuation of application No. 16/553,069, filed on Aug. 27, 2019, now Pat. No. 11,419,936, which is a division of application No. 15/211,881, filed on Jul. 15, 2016, now Pat. No. 10,434,176, which is a continuation of application No. 13/581,245, filed as application No. PCT/EP2011/052770 on Feb. 24, 2011, now Pat. No. 9,422,364.

(60) Provisional application No. 61/282,548, filed on Feb. 26, 2010.

(30) Foreign Application Priority Data

Feb. 26, 2010     (EP) ..................................... 10001996

(51) Int. Cl.
| | |
|---|---|
| *A61K 39/395* | (2006.01) |
| *A61K 9/00* | (2006.01) |
| *C07K 16/06* | (2006.01) |
| *A61K 39/00* | (2006.01) |

(52) U.S. Cl.
CPC ...... *A61K 39/39591* (2013.01); *A61K 9/0019* (2013.01); *A61K 39/395* (2013.01); *C07K 16/06* (2013.01); *A61K 2039/54* (2013.01); *C07K 2317/21* (2013.01); *C07K 2317/35* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 4,186,192 A | 1/1980 | Lundblad et al. |
| 4,360,451 A | 11/1982 | Schmolka |
| 4,362,661 A | 12/1982 | Ono et al. |
| 4,396,608 A | 8/1983 | Tenold |
| 4,439,421 A | 3/1984 | Hooper et al. |
| 4,499,073 A | 2/1985 | Tenold |
| 4,727,027 A | 2/1988 | Wiesehahn et al. |
| 4,849,508 A | 7/1989 | Magnin et al. |
| 4,880,913 A | 11/1989 | Doleschel et al. |
| 5,164,487 A | 11/1992 | Kothe et al. |
| 5,177,194 A | 1/1993 | Sarno et al. |
| 5,503,827 A | 4/1996 | Woog et al. |
| 5,593,675 A | 1/1997 | Hodler et al. |
| 5,871,736 A | 2/1999 | Bruegger et al. |
| 5,945,098 A | 8/1999 | Sarno et al. |
| 6,069,236 A | 5/2000 | Burnouf-Radosevich et al. |
| 6,093,324 A | 7/2000 | Bertolini et al. |
| 6,162,904 A | 12/2000 | Mamidi et al. |
| 6,171,586 B1 | 1/2001 | Lam et al. |
| 6,252,055 B1 | 6/2001 | Relton |
| 6,303,113 B1 | 10/2001 | Woog et al. |
| 8,715,652 B2 | 5/2014 | Bolli et al. |
| 9,241,897 B2 | 1/2016 | Bolli |
| 9,422,364 B2 | 8/2016 | Maeder et al. |
| 10,137,197 B2 | 11/2018 | Bolli et al. |
| 10,434,176 B2 | 10/2019 | Maeder et al. |
| 12,144,861 B2 * | 11/2024 | Pedrussio ............... A61P 25/00 |
| 2005/0142139 A1 | 6/2005 | Schulke et al. |
| 2007/0122402 A1 | 5/2007 | Bolli et al. |
| 2008/0275220 A1 | 11/2008 | Friess et al. |
| 2012/0308557 A1 | 12/2012 | Bolli et al. |
| 2013/0102760 A1 | 4/2013 | Bolli et al. |

FOREIGN PATENT DOCUMENTS

| | | |
|---|---|---|
| AU | 2004290899 B2 | 3/2010 |
| CA | 2272245 | 5/1998 |
| DE | 2 364 792 | 7/1974 |
| DE | 3 430 320 | 3/1985 |
| DE | 4 118 912 | 7/1992 |

(Continued)

OTHER PUBLICATIONS

Opponent Grifols, S.A.'s response to Proprietor's Letter, filed Jun. 10, 2014, for European Patent No. 1687028 B1 (Application No. 04818790.0-1412) (20 pages).

A.W.P. Vermeer et al., "The Thermal Stability of Immunoglobulin: Unfolding and Aggregation of a Multi-Domain Protein," Biophys. J., 78: 394-404 (2000), Document D24 submitted Jun. 10, 2014, with Opponent's Response to Proprietor's Letter, for European Patent No. 1687028 B1 (Application No. 04818790.0-1412).

W.R. Gombotz et al., "The Stabilization of a Human IgM Monoclonal Antibody with Poly(vinylpyrrolidone)," Pharm. Res., 11(5): 624-632 (1994), Document D25 submitted Jun. 10, 2014, with Opponent's Response to Proprietor's Letter, for European Patent No. 1687028 B1 (Application No. 04818790.0-1412).

(Continued)

*Primary Examiner* — Yunsoo Kim
(74) *Attorney, Agent, or Firm* — McNeill PLLC

(57)     ABSTRACT

The present invention relates to an immunoglobulin preparation comprising immunoglobulin in a mass-volume percentage of at least 4%, wherein the concentration of oxygen dissolved in the preparation at room temperature is less than 40 µmol/l.

20 Claims, 3 Drawing Sheets

(56) References Cited

FOREIGN PATENT DOCUMENTS

Figure 1:
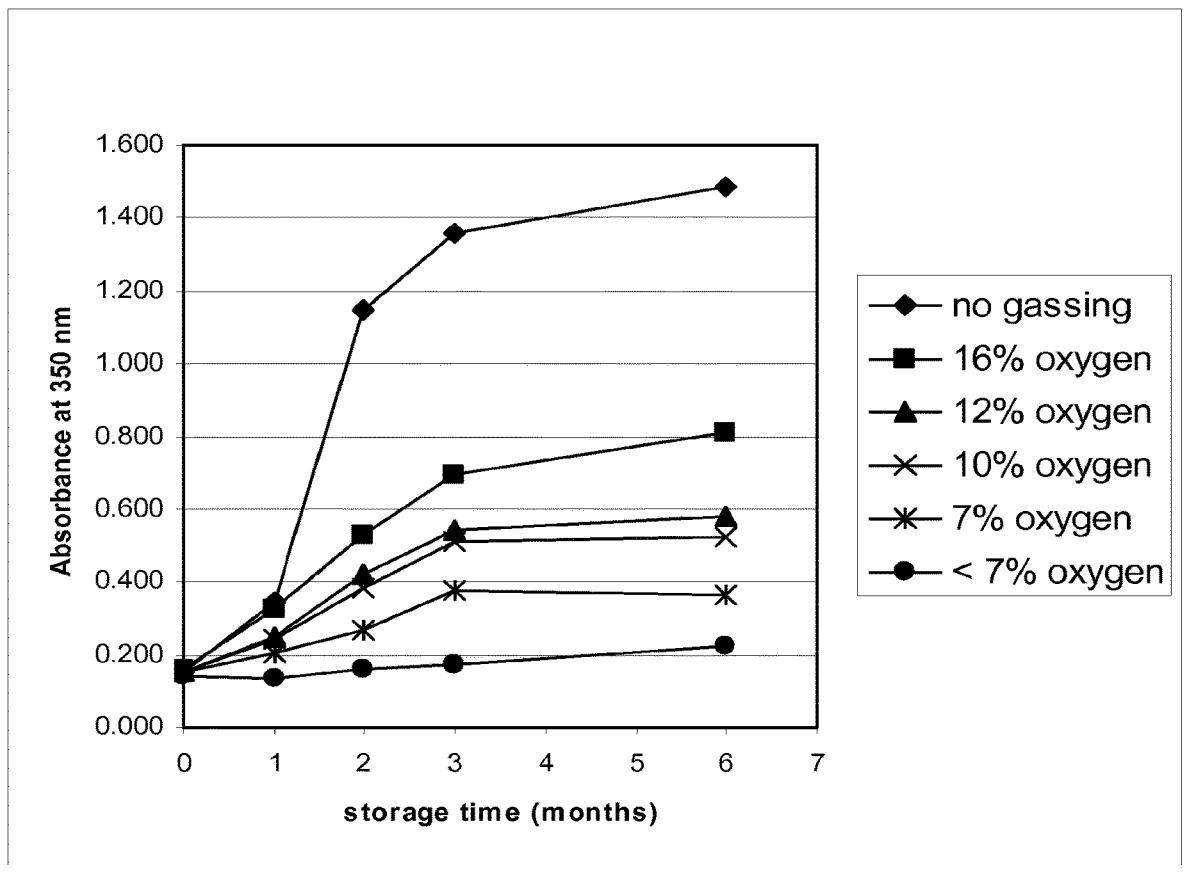

| EP | 0 025 275 | 3/1981 |
| EP | 0 037 078 | 10/1981 |
| EP | 0 187 712 | 7/1986 |
| EP | 0 196 761 | 10/1986 |
| EP | 0 392 717 | 10/1990 |
| EP | 0 437 622 | 7/1991 |
| EP | 0 528 313 | 2/1993 |
| EP | 0 447 585 | 5/1995 |
| EP | 0 702 960 | 3/1996 |
| EP | 0 852 951 | 7/1998 |
| EP | 0 893 450 | 1/1999 |
| EP | 0 911 037 | 4/1999 |
| EP | 1 268 551 | 2/2004 |
| EP | 1 084 147 | 9/2004 |
| EP | 1 532 983 | 5/2005 |
| EP | 2538975 B1 | 9/2019 |
| JP | S54-20124 | 2/1979 |
| JP | S56-127321 | 10/1981 |
| JP | S57-31623 | 2/1982 |
| JP | S57-128635 | 8/1982 |
| JP | 60-120823 | 6/1985 |
| JP | 61-194035 | 8/1986 |
| JP | H04-346934 | 12/1992 |
| JP | 05-178719 | 7/1993 |
| JP | H06-510031 | 11/1994 |
| JP | H08-99899 | 4/1996 |
| JP | H10-502938 | 3/1998 |
| JP | H11-502833 A | 3/1999 |
| JP | 2001-503781 | 3/2001 |
| JP | 2001-519770 | 10/2001 |
| JP | 2004-225416 B2 | 12/2008 |
| JP | 2009-5263080 A | 7/2009 |
| WO | WO 94/29334 | 12/1994 |
| WO | WO 96/07429 | 3/1996 |
| WO | WO 96/15153 | 5/1996 |
| WO | WO 96/30041 A1 | 10/1996 |
| WO | WO 98/05686 | 2/1998 |
| WO | WO 98/28007 | 7/1998 |
| WO | WO 99/64462 | 12/1999 |
| WO | WO 02/080976 | 10/2002 |
| WO | WO 03/002139 A1 | 10/2003 |
| WO | WO 2004/084816 | 10/2004 |
| WO | WO 2005/049078 | 6/2005 |
| WO | 2007092620 A2 | 8/2007 |
| WO | WO 2007/092829 A2 | 8/2007 |
| WO | WO 2008/039761 | 4/2008 |
| WO | WO 2011/095543 A1 | 8/2011 |

OTHER PUBLICATIONS

Certified priority document EP Patent App. No. 03026539.1, filed Nov. 18, 2003 (27 pages), Document D26 submitted Jun. 10, 2014, with Opponent's Response to Proprietor's Letter, for European Patent No. 1687028 B1 (Application No. 04818790.0-1412).

"2.2.2. Degree of Coloration of Liquids," from European Pharmacopoeia 5.0, Supplement 5.5, pp. 24-26, Jul. 2006.

Summons to attend oral proceedings pursuant to Rule 115(1) EPC, mailed Jun. 13, 2014, for EP Patent No. 1687028 (17 pages).

Supplemental Proprietor's submission filed Apr. 17, 2014, for European Patent No. 1687028 B1 (Application No. 04818790.0-1412) (7 pages).

Australian Patent Examination Report No. 2; Application No. 2011219828 dated Sep. 3, 2014.

"Peptide Storage and Handling Guidelines" GenScript, the Biology CRO, (2010).

Notice of Allowance and Fee(s) Due, mailed Aug. 5, 2014, for U.S. Appl. No. 13/618,757 (7 pages).

Communication pursuant to Article 94(3) EPC for EP Patent App. No. 10177786.0 (3 pages).

Patent Owner's Response to Notice of Opposition submitted Mar. 7, 2014, for European Patent No. 1687028 B1 (Application No.

04818790.0-1412) (30 pages), including transmittal letter of Carpmaels & Ransford, submission list, observations, and main request claims (13 pages).

International Blood Plasma News Apr. 2010—Privigen (1 page), Document D17 submitted Mar. 7, 2014, with Patent Owner's Response to Notice of Opposition submitted Mar. 7, 2014, for European Patent No. 1687028 B1 (Application No. 04818790.0-1412).

CSL Behring press release of Feb. 24, 2011 (2 pages), Document D18 submitted Mar. 7, 2014, with Patent Owner's Response to Notice of Opposition submitted Mar. 7, 2014, for European Patent No. 1687028 B1 (Application No. 04818790.0-1412).

Letter from EMEA concerning Hizentra (3 pages), Document D19 submitted Mar. 7, 2014, with Patent Owner's Response to Notice of Opposition submitted Mar. 7, 2014, for European Patent No. 1687028 B1 (Application No. 04818790.0-1412).

Letter from US FDA concerning Hizentra (2 pages), Document D20 submitted Mar. 7, 2014, with Patent Owner's Response to Notice of Opposition submitted Mar. 7, 2014, for European Patent No. 1687028 B1 (Application No. 04818790.0-1412).

Transmittal of Labels and Circulars Mar. 28-29, 2010 from US FDA concerning Privigen (1 page), Document D21 submitted Mar. 7, 2014, with Patent Owner's Response to Notice of Opposition submitted Mar. 7, 2014, for European Patent No. 1687028 B1 (Application No. 04818790.0-1412).

Declaration of Annette Gaida (7 pages), Document D22 submitted with Patent Owner's Response to Notice of Opposition submitted Mar. 7, 2014, for European Patent No. 1687028 B1 (Application No. 04818790.0-1412).

European Search Report dated Apr. 28, 2004, for European Patent Application No. 03026539.1 (10 pages).

PCT International Search Report and Written Opinion mailed May 27, 2005, for International Patent Application No. PCT/EP2004/013022 (15 pages).

Notice of the Reason of Rejection dispatched Jul. 13, 2010, for Japanese Patent Application No. 2006-540301 (3 pages) with translation (4 pages).

Office Action dated Jan. 4, 2011, for Canadian Patent Application No. 2,545,939 (3 pages).

Extended European Search Report dated May 4, 2012, for European Patent Application No. 10177786.0 (9 pages).

Notice of Opposition dated Jun. 28, 2013, for European Patent No. 1687028 (21 pages).

T. Arakawa et al., "The Stabilization of Proteins by Osmolytes," Biophys. J., 47: 411-414, (1985).

T. Arakawa et al., "Protein-Solvent Interactions in Pharmaceutical Formulations," Pharmaceutical Research, 8(3): 285-291 (1991).

W.K. Bleeker et al., "An Animal Model for the Detection of Hypotensive Side Effects of Immunoglobulin Preparations," Vox Sang., 52: 281-290 (1987).

J.F. Carpenter et al., "Cryoprotection of Phosphofructokinase with Organic Solutes: Characterization of Enhanced Protection in the Presence of Divalent Cations," Archives of Biochemistry and Biophysics, 250(2): 505-512 (1986).

K.C. Hazen et al., "Cryoprotection of Antibody by Organic Solutes and Organic Solute/Divalent Cation Mixtures," Archives of Biochemistry and Biophysics, 267(1): 363-371 (1988).

D.A. Parkins et al., "The Formulation of Biopharmaceutical Products," Pharmaceutical Science & Technology Today, 3(4): 129-137 (2000).

D. Samuel et al., "Proline is a Protein Solubilizing Solute," Biochemistry and Molecular Biology International, 41(2): 235-242 (1997).

D. Samuel et al., "Proline Inhibits Aggregation During Protein Refolding," Protein Science, 9: 344-352 (2000).

L.T. Smith "Characterization of a .gamma.-Glutamyl Kinase from *Escherichia coli* That Confers Proline Overproduction and Osmotic Tolerance," Journal of Bacteriology, 164(3): 1088-1093 (1985).

S. Taneja et al., "Increased Thermal Stability of Proteins in the Presence of Amino Acids," Biochem. J., 303: 147-153 (1994).

D.L. Tankersley et al., "Immunoglobulin G Dimer: An Idiotype-Anti-Idiotype Complex," Molecular Immunology, 25(1): 41-48 (1988).

(56) References Cited

OTHER PUBLICATIONS

U.S. Department of Health and Human Services, Food and Drug Administration, Center for Drug Evaluation and Research (CDER), Center for Biologics Evaluation and Research (CBER), "Guidance for Industry Q1A(R2) Stability Testing of New Drug Substances and Products, Revision 2," Nov. 2003 (25 pages).

Notification of Transmittal of the International Search Report and the Written Opinion of the International Searching Authority, or the Declaration, for International Patent App. No. PCT/EP2011/052770, mailed Jun. 9, 2011 (9 pages).

Extended European Search Report and European Search Opinion for European Patent App. No. 10 001 996.7, mailed Aug. 6, 2010 (5 pages).

J.L. Cleland et al., "The Development of Stable Protein Formulations: A Close Look at Protein Aggregation, Deamidation, and Oxidation," Crit. Rev. Therap. Drug Carrier Systems, 10(4): 307-377 (1993).

P. Qi et al., "Characterization of the Photodegradation of a Human IgG1 Monoclonal Antibody Formulated as a High-concentration Liquid Dosage form," J. Pharm. Sci., 98(9): 3117-3130 (2009).

Decision on Appeal, mailed Dec. 9, 2013 for U.S. Appl. No. 10/579,357.

Record of Oral Hearing, mailed Jan. 24, 2014, for U.S. Appl. No. 10/579,357.

Notice of Allowance and Fee(s) Due, mailed Dec. 19, 2013, for U.S. Appl. No. 10/579,357.

Rejection Decision, mailed May 8, 2014, for Chinese Patent App. No. 201180010874.X (4 pages), with translation (4 pages).

Non-final Office Action, mailed Dec. 26, 2013, for U.S. Appl. No. 13/618,757.

Reply to Office Action, filed Mar. 14, 2014, for U.S. Appl. No. 13/618,757.

Final Office Action, mailed May 23, 2014, for U.S. Appl. No. 13/618,757.

R. Bolli et al., "L-Proline reduces IgG dimer content and enhances the stability of intravenous immunoglobulin (IVIG) solutions," Biologicals, 38: 150-157 (2010).

M. Cramer et al., "Stability over 36 months of a new liquid 10% polyclonal immunoglobulin product (IgPro10, Privigen ©) stabilized with L-proline," Vox Sanguinis, 96: 219-225 (2009).

S. Misbah et al., "Subcutaneous immunoglobulin: opportunities and outlook," Clinical and Experimental Immunology, 158 (Suppl. 1): 51-59 (2009).

Notification of Transmittal of the International Search Report and the Written Opinion of the International Searching Authority, or the Declaration, for International Patent App. No. PCT/EP2011/051556, mailed Feb. 28, 2011 (15 pages).

Extended European Search Report and European Search Opinion for European Patent App. No. 10 001 164.2, mailed Jul. 19, 2010 (10 pages).

U.S. Food and Drug Administration package insert for Hizentra, Immune Globulin Subcutaneous (Human), 20% Liquid, issued Feb. 2010 (26 pages).

U.S. Food and Drug Administration package insert for Privigent™, Immune Globulin Intravenous (Human), 10% Liquid, issued Jul. 2007 (20 pages).

International Blood/Plasma News, "CSL Behring announced that the U.S. FDA has approved a supplemental Biologics License Application (sBLA) that extends the shelf life of its Privigen 10% liquid intravenous immunoglobulin product from 24 months to 36 months," p. 12, Apr. 2010.

D.L. Tankersley, "Dimer Formation in Immunoglobulin Preparations and Speculations on the Mechanism of Action of Intravenous Immune Globulin in Autoimmune Diseases," Immunological Reviews 139: 159-172 (1994).

CSL Behring press release, "CSL Behring Receives FDA Approval to Extend Shelf Life of Hizentra™ from18 months to 24 months," Aug. 18, 2010 (2 pages).

H. Lilie, "Folding of the Fab fragment within the intact antibody," FEBS Lett. 417: 239-242 (1997).

M.O. Spycher et al., "Well-tolerated liquid intravenous immunoglobulin G preparations (IVIG) have a low immunoglobulin G dimer (IgG-dimer) content," J. Autoimmun. 96 (Suppl. 1): 96 (1996).

R. Bolli et al. "IgG-dimer formation in liquid immunoglobulin preparations is inhibited by nicotinamide and other amphiphilic compounds," J. Autoimmun. 96 (Suppl. 1): 96 (1996).

G. Lemm, "Composition and properties of IVIg preparations that affect tolerability and therapeutic efficacy," Neurology 59(Suppl. 6): S28-S32 (2002).

W. Wang, "Instability, stabilization, and formulation of liquid protein pharmaceuticals," Int. J. Pharmaceutics 185: 129-188 (1999).

B. Alberts et al., Molecular Biology of the Cell 3.sub.rd Ed. 1994, cover pages and p. G-12.

A.K. Abbas et al., Cellular and Molecular Immunology 4.sup.th Ed. 2000, cover pages and pp. 470 and 482.

I. Andresen et al., "Product equivalence study comparing the tolerability, pharmacokinetics, and pharmacodynamics of various human immunoglobulin-G formulations," J. Clin Pharmacol, vol. 40, pp. 722-730 (2000).

T.K.S. Kumar et al., "The Role of Proline in the Prevention of Aggregation During Protein Folding In Vitro," Biochem. Mol. Biol. Int., 46(3): 509-517 (1998).

K. Shiraki et al. "Biophysical Effect of Amino Acids on the Prevention of Protein Aggregation," J. Biochem., 132(4): 591-595 (2002).

English Language Derwent abstract of JP 05-178719 A, 1980.

English Language Derwent abstract of JP 60-120823 A, 1985.

English Language Derwent abstract of JP 61-194035 A, 1994.

I. Andersson et al., "An Improved Chromatography Method for Production of IgG from Human Plasma," Presented at XXIII Congress of the International Society of Blood Transfusion (1994).

J.-P. Azulay et al., "Intravenous Immunoglobulin Treatment in Patients With Motor Neuron Syndromes Associated With Anti-GM.sub.1 Antibodies, a Double-Blind, Placebo-Controlled Study," Neurology, 44: 429-432 (1994).

M. Basta et al., "High-Dose Intravenous Immunoglobulin Exerts its Beneficial Effect in Patients with Dermatomyositis by Blocking Endomysial Deposition of Activated Complement Fragments," J. Clin. Invest., 94: 1729-1735 (1994).

S.A. Berkman et al., "Clinical Uses of Intravenous Immunoglobulins," Annals Internal Medicine, 112: 278-292 (1990).

L. Biesert, "Virus Validation Studies of Immunoglobulin Preparations," Clin. Exp. Rheumatol., 14(Suppl. 15): S47-S52 (1996).

J. Bjorkander et al., "1040 Prophylactic Infusions with an Unmodified Intravenous Immunoglobulin Product Causing Few Side-Effects in Patients with Antibody Deficiency Syndromes," Infection, 13(3): 102-110 (1985).

B. Brenner, "Clinical Experience With Octagam, a Solvent Detergent (SD) Virus Inactivated Intravenous Gammaglobulin," Clin. Exp. Rheumatol., 14(Suppl. 15): S115-S119 (1996).

R.H. Buckley et al., "The Use of Intravenous Immune Globulin in Immunodeficiency Diseases," New Eng. J. Med., 325(2): 110-117 (1991).

P. Cassulis et al., "Ligand Affinity Chromatographic Separation of Serum IgG on Recombinant Protein G-Silica," Clin. Chem., 37(6): 882-886 (1991).

M.-F. Clerc et al., "Labelling of Colloidal Gold with IgE," Histochemistry, 89: 343-349 (1988).

Cooperative Group for the Study of Immunoglobulin in Chronic Lymphocytic Leukemia, "Intravenous Immunoglobulin for the Prevention of Infection in Chronic Lymphocytic Leukemia, a Randomized, Controlled Clinical Trial," New Eng. J. Med., 319: 902-907 (1998).

M.C. Dalakas, "Intravenous Immune Globulin Therapy for Neurologic Diseases," Ann. Int. Med., 126(9): 721-730 (1997).

J.M. Dwyer, "Manipulating the Immune System with Immune Globulin," New Eng. J. Med., 326(2): 107-116 (1992).

S. El Alaoui et al., "Development of an Immunocapture Method for Measuring IgA Antibodies to Tissue Transglutaminase in the Sera of Patients with Coeliac Disease," Clin. Exp. Immunol., 144: 101-109 (2006).

(56)                    References Cited

OTHER PUBLICATIONS

Gammagard S/D, "Humanes Immunoglobulin Zur Intravenosen Anwendung Solvent/Detergent Behandelt," Product Information, Baxter Deutschland GmbH, Edisonstr. 3-4, D-85716 Unterschleibheim, Germany (1994).

A.F.S.A. Habeeb et al., "Preparation of Human Immunoglobulin by Caprylic Acid Precipitation," Preparative Biochem., 4(1): 1-17 (1984).

P. Hansen et al., "Isolation and Purification of Immunoglobulins from Chicken Eggs Using Thiophilic Interaction Chromatography," J. Immunol. Meth., 215: 1-7 (1998).

J.R. Harris, Ed., "Blood Separation and Plasma Fractionation," pp. 332-333, Wiley-Liss, New York (1991).

H. Hocini et al., "An Elisa Method to Measure Total and Specific Human Secretory IgA Subclasses Based on Selective Degradation by IgA1-Protease," J. Immunol. Meth., 235(1-2): 53-60 (2000) (Abstract).

S.-V. Kaveri et al., "Intravenous Immunoglobulins (IVIg) in the Treatment of Autoimmune Diseases," Clin. Exp. Immunol., vol. 86, pp. 192-198 (1991).

W.J. Koopman et al., "A Sensitive Radioimmunoassay for Quantitation of IgM Rheumatoid Factor," Arth. Rheum., 23(3): 302-308 (1980).

J.L. Lundblad et al., "Comparative Studies of Impurities in Intravenous Immunoglobulin Preparations," The University of Chicago, Rev. Infectious Diseases, 8(Supp. 4): S382-S390 (1986).

J.P. McCue, "Changes in Therapeutic Proteins Caused by Preparation Techniques," Ann. Internal Medicine, 111(4): 271-272 (1989).

T.E. Mollnes et al., "Effect of Whole and Fractionated Intravenous Immunoglobulin on Complement In Vitro," Mol. Immunol., 34(10): 719-729 (1997).

N. Nourichafi et al., "Comparison of various chromatographic supports for purifying human plasmatic immunoglobulins from Cohn II+III fraction," Biotech. Blood Proteins, 227: 207-212 (1993).

U.E. Nydegger, "Sepsis and Polyspecific Intravenous Immunoglobulins," J. Clin. Apheresis, 12: 93-99 (1997).

G. Oldham et al., "A Quantitative Method for Measuring in vitro Synthesis of IgA and IgG by Human Rectal Mucosa: Studies on normal controls and patients with hypogammaglobulinaemia," Immunol., 37: 661-668 (1979).

R.K. Scopes, "Protein Purification, Principles and Practice," 2nd Edition, pp. 42-45, in "Springer Advance Texts in Chemistry," Charles R. Cantor Ed., Springer-Verlag, N.Y. (1987).

M. Stucki et. al., "Characterisation of a Chromatographically Produced Anti-D Immunoglobulin Product," J. Chromatograph B., 700: 241-248 (1997).

F.B. Waldo et al., "Mixed IgA-IgG Aggregates as a Model of Immune Complexes in IgA Nephropathy," J. Immunol., 142(11): 3841-3846 (1989).

W. Wang, "Antibody Structure, Instability, and Formulation," J. Pharm. Sci., 96(1): 1-26 (2007).

J.V. Wells et al., "Cord Serum IgA Levels in Australian Infants," J. Paediatrics Child Health, 16(3): 189-90 (1980) (Abstract).

English Language Derwent abstract of DE 2 364 792, 1974.

English Language Derwent abstract of DE 3 430 320 A1, 1985.

English Language Derwent abstract of DE 4 118 912 C1, 1992.

Restriction Requirement mailed May 12, 2008, for U.S. Appl. No. 10/579,357.

Response to Restriction Requirement, filed Jun. 12, 2008, for U.S. Appl. No. 10/579,357.

Office Action, mailed Sep. 26, 2008, for U.S. Appl. No. 10/579,357.

Response to Office Action, filed Feb. 9, 2009, for U.S. Appl. No. 10/579,357.

Final Office Action, mailed May 5, 2009, for U.S. Appl. No. 10/579,357.

Amendment and Response under 37 C.F.R § 1.116, filed Aug. 4, 2009, for U.S. Appl. No. 10/579,357.

Advisory Action, mailed Aug. 7, 2009, for U.S. Appl. No. 10/579,357.

Request for Continued Examination, filed Sep. 3, 2009, for U.S. Appl. No. 10/579,357.

Office Action, mailed Nov. 16, 2009, for U.S. Appl. No. 10/579,357.

Reply to Office Action, filed Feb. 16, 2010, for U.S. Appl. No. 10/579,357.

Final Office Action, mailed May 19, 2010, for U.S. Appl. No. 10/579,357.

Interview Summary, mailed Aug. 19, 2010, for U.S. Appl. No. 10/579,357.

Request for Continued Examination and Reply to Office Action under 37 C.F.R. § 1.114, filed Sep. 17, 2010, for U.S. Appl. No. 10/579,357.

Office Action, mailed Jun. 7, 2010, for U.S. Appl. No. 10/579,357.

Notice of Appeal under 37 C.F.R. § 41.31, filed Sep. 7, 2011, for U.S. Appl. No. 10/579,357.

Appeal Brief under Board Rule § 41.37, filed Oct. 3, 2011, for U.S. Appl. No. 10/579,357.

Examiner's Answer, mailed Dec. 21, 2011, for U.S. Appl. No. 10/579,357.

Reply Brief under Board Rule § 41.41 and Request for Oral Hearing, filed Feb. 21, 2012, for U.S. Appl. No. 10/579,357.

Information Provision by the third party, submitted Apr. 13, 2016, for Japanese Patent Application No. 2012-554344, including English translation, (10 pages).

A.L. Daugherty et al., Advanced Drug Delivery Reviews 58: 686-706 (2006).

Notice of Allowance and Notice of Allowability, Sep. 16, 2015, U.S. Appl. No. 13/577,220.

Letter from Opponent in Opposition against European Patent No. 1687028, Sep. 24, 2014 (3 pages).

Rule 116 Submission and Response to Opponent's Further Submission and cover letter in Opposition against European Patent No. 1687028, Sep. 26, 2014 (11 pages).

Interlocutory Decision in Opposition Proceedings dated Dec. 10, 2014 in Opposition against European Patent No. 1687028 (application No. 04 818 790.0) (7 pages).

Interlocutory Decision in Opposition Proceedings dated Jan. 20, 2015 in Opposition against European Patent No. 1687028 (application No. 04 818 790.0) (11 pages).

Duenas et al. "Comparison between Light Induced and Chemically Induced Oxidation of rh CEGF," *Pharmaceutical Research*, 18(10): 1455-1460 (2001).

Davies and Truscott "Photo-oxidation of proteins and its role in cataractogenesis," *Journal of Photochemistry and Photobiology B*, 63: 114-125 (2001).

W. Maeder et al., "Local tolerance and stability up to 24 months of a new 20% prolinestabilized polyclonal immunoglobulin for subcutaneous administration," Biologicals, 39: 43-49 (2011).

Summons to attend oral proceedings pursuant to Rule 115(1) EPC, mailed Jul. 5, 2018, for EP Patent Application No. 11707382.5 (11 pages).

Prosecution history of U.S. Appl. No. 15/211,881, filed Jul. 15, 2016.

ICH Guideline; ICH Topic Q 1 A (R2) Stability Testing of new Drug Substances and Products, Aug. 2003, European Medicines Agency, 20 pages.

Trivedi, Maulik V. et al., "The role of thiols and disulfides in protein chemical and physical stability", Curr Protein Pept Sci. Dec. 2009; 10(6) 614-625.

Cannell, John S. et al., "Fundamentals of stability testing", International Journal of Cosmetic Science 7, 291-303 (1985).

Extended European Search Report issued in EP Application No. 19193100.5, mailed Dec. 17, 2019 (3 pages).

Kroez et al., "Hypotension with intravenous immunoglobulin therapy: importance of pH and dimer formation", Biologicals, 31, pp. 277-286 (2003).

Maeder et al., "Stability of 24 Months and Tolerability of a New 20% Proline-stabilized Polyclonal Immunoglobulin for Subcutaneous Administration (SCIG)", J. Allergy Clin Immunol. AB142 Abstracts (Feb. 2010).

"2.2 Physical and Physicochemical Methods", European Pharmacopoeia, pp. 15-17 (1997).

"Human Normal Immunoglobulin for Intravenous Administration", European Pharmacopoeia, 1997:0918, pp. 963-965.

(56) References Cited

OTHER PUBLICATIONS

CSL Behring GmbH's submission to the EPO Examining Division dated Dec. 11, 2018 (45 pages).
CSL Behring GmbH's submission to the EPO Examining Divisional dated Feb. 1, 2019 (43 pages).
Gammagard S/D, "Immune Globulin Intravenous (Human), Solvent Detergent Treated" (Aug. 2002) (20 pages).
Gammagard S/D, Package Insert (May 2015) (7 pages) (German).
Gammanorm (Injektionslosung), data sheet (Apr. 2005) (7 pages).
P&T Product Profiler, "Immune Globulin Subcutaneous (Human) Vivaglobin", 34:6 (Jun. 2009) (28 pages).
Wang et al., "Lyophilization and development of solid protein pharmaceuticals", Int J. Pharm, 203(1-2) pp. 1-60 (2000).
Tempelton et al., "Rapid Headspace Oxygen Analysis for Pharmaceutical Packaging Applications", Pharmaceutical Technology, pp. 44-61 (Jul. 2002).
Rao et al., "Chemical Mechanisms and Functional Effects of Degradation of a Therapeutic Monoclonal Antibody", Chapter 4 of Stability and Characterization of Protein and Peptide Drugs Case Histories, pp. 135-158 (2013).
U.S. Appl. No. 61/225,455, filed Jul. 14, 2009.
Notice of Opposition to EP2538975B1, submitted Jun. 18, 2020 (35 pages).
Citation list in Opposition of EP2538975B1, dated Jun. 18, 2020 (1 page).
Reply of Proprietor in Opposition of EP2538975B1, dated Nov. 10, 2020 (19 pages).
Main Request of Proprietor in Opposition of EP2538975B1, dated Nov. 10, 2020 (1 page).
Prosecution history of U.S. Appl. No. 13/581,245, filed Sep. 18, 2012.
Prosecution history of U.S. Appl. No. 16/553,069, filed Aug. 27, 2019.
Haven, Mary C. et al., "Laboratory Instrumentation" Fourth Edition, John Wiley & Songs, Inc. 1995, p. 90.
Patentee Observations Submission in European Patent No. 2538975, dated Nov. 10, 2020, 18 pages.
Patentee Submission in European Patent No. 2538975, dated Sep. 21, 2023, 6 pages.
Patentee's Rule 116 EPC Submission in European Patent No. 2538975, dated Mar. 14, 2023, 6 pages.
"Human Normal Immunoglobulin for Subcutaneous Administration", European Pharmacopoeia, Jan. 2015:2788, pp. 4351-4353.

* cited by examiner

IMMUNOGLOBULIN PREPARATION AND STORAGE SYSTEM FOR AN IMMUNOGLOBULIN PREPARATION

This application is a continuation of U.S. application Ser. No. 16/553,069, filed Aug. 27, 2019, which is a divisional of U.S. application Ser. No. 15/211,881, filed Jul. 15, 2016, which is a continuation of U.S. application Ser. No. 13/581, 245, which has a 35 USC Section 371 (c) date of Sep. 18, 2012, and which is the US national stage of International Application No. PCT/EP2011/052770, filed Feb. 24, 2011, which claims priority to European Patent Application No. 10 001 996.7, filed Feb. 26, 2010, and U.S. Provisional Application No. 61/282,548, filed Feb. 26, 2010, all of which are incorporated herein by reference.

The present invention relates to an immunoglobulin (Ig) preparation with improved stability for storage.

The invention further relates to a storage system for the Ig preparation, to a process for providing such a storage system and to the use of a gas having an oxygen content of less than 20 vol-% for increasing the storage stability of an Ig preparation.

Ig preparations for Ig replacement therapy, e.g. for the treatment of primary immunodeficiency (PID) disorders, such as common variable immunodeficiency (CVID) and X-linked agammaglobulinemia, are widely known in the art. Such Ig preparations are commonly obtained from human plasma and are stored in vials for further use. The preparation can then be administered intravenously (IVIg) or subcutaneously (SCIg) to the patient in need of the therapy.

When using the subcutaneous route, Ig preparations having a relatively high Ig concentration are desirable, since they allow for a less frequent administration and/or an administration of smaller volumes than a preparation of lower concentration.

If stored over several months, known Ig preparations tend to become yellowish in colour. This effect is particularly pronounced for Ig preparations having a relatively high Ig concentration and exposed to stress conditions like light exposure and/or elevated temperature; said preparations typically show a relatively strong, yellow-brownish coloration already after storage of two months.

Such a coloration is however in conflict to standard requirements for Ig preparations. The European Pharmacopoeia, for example, requires the preparation to remain clear-yellow or light brown.

One possible approach to cope with this problem is to store the Ig preparation in a dark environment. A further approach is to store the Ig preparation at a relatively low temperature, for example at about 5° C. Although both approaches have shown to result in a reduction of yellowish coloration, they are inconvenient for the handling and are relatively burdensome to put into practice, since the respective environment has to be maintained over the whole storage period.

It is therefore an object of the present invention to provide an Ig preparation for Ig replacement therapy, which shows a reduced yellowish coloration and thus allows for complying with the standard requirements concerning coloration even after prolonged storage under light and under room temperature. It is a further object to provide a storage system for storing the preparation in a manner such that the yellowish coloration is reduced, thus allowing for complying with the standard requirements concerning coloration even after prolonged storage under stress conditions like exposure to light and/or elevated temperature.

The problem is solved by the Ig preparation and the storage system according to the independent claims. Preferred embodiments are subject of the dependent claims.

According to a first aspect, the present invention thus relates to an Ig preparation comprising Ig in a mass-volume percentage of at least 4% (i.e. 4 g/100 ml). In contrast to naturally occurring biological fluids, the liquid Ig preparation of the present invention is thus enriched in Ig. Given its relatively high Ig concentration, the preparation is suitable for Ig replacement therapy. Preparations of 10% or more are suitable for subcutaneous administration which may be performed by the patients themselves.

It has surprisingly been found that if the concentration of oxygen dissolved in the preparation at room temperature is less than 200 μmol/l, a high stability against yellowish coloration over a prolonged period of time can be achieved. Preferably, the yellowish coloration is caused by stress factors other than light exposure, i.e. occurs in the dark, is not caused by photodegradation. In particular, a stable Ig preparation showing only a slight yellowish coloration or no yellowish coloration at all can be achieved, thus meeting standard requirements, e.g. of the European Pharmacopoeia, even after a prolonged storage period of 24 months, even of 36 months, or longer. In particular, a stable Ig preparation meeting the standard requirements can be achieved, even after a prolonged storage period of 24 months, even of 36 months, at room temperature in the dark. The absorbance $A_{350-500nm}$ of the stable immunoglobulin preparation remains below 0.28 upon storage for 24 months at 25° C. in the dark, preferably the stable immunoglobulin preparation has a concentration of 20% w/v. In a preferred embodiment of the invention, the absorbance $A_{350-500nm}$ remains below 0.355 when measured for a 20% Ig preparation after storage for 6 months at 37° C. in the dark. The stable immunoglobulin preparation shows an increase in $A_{350-500nm}$ of less than 0.18, preferably of less than 0.17, even more preferably of less than 0.16, when stored at 25° C. in the dark for 36 months. The stable immunoglobulin preparation shows an increase in $A_{350-500nm}$ of less than 0.22, preferably of less than 0.20, even more preferably of less than 0.19, when stored at 37° C. in the dark for 6 months.

Methods for determining the concentration of oxygen dissolved in the Ig preparation are well known to the skilled person. For example, the oxygen concentration can be determined by a polarographic method, using e.g. a Clark electrode. Alternatively, also luminescence oxygen sensing can for example be used for determining the oxygen concentration in the preparation.

When contained in a container, the Ig preparation's oxygen concentration can be determined using an electrode extending into the container and into the Ig preparation contained therein. Alternatively, the Ig preparation's oxygen concentration can be determined after opening of the container. In this latter case, determination is carried out within 5 minutes after opening of the container in order to avoid corruption of the respective result by an increase of the oxygen content of the gas which is in contact with the immunoglobulin preparation.

Without wanting to be bound by the theory, it is assumed that the yellowish coloration typically seen with conventional Ig preparations is due to an oxidative alteration of the Ig contained therein. According to the present invention, this oxidative alteration is reduced by maintaining the amount of oxygen dissolved in the preparation at a concentration lower than the concentration that would be established if the preparation is stored under air at atmospheric pressure.

Given the fact that according to the present invention an Ig preparation can be obtained, which even after prolonged storage shows only a slight yellowish coloration or no yellowish coloration at all, both patients and physicians can readily acknowledge that the Ig contained therein is in good quality, which further contributes to an increase in the acceptance of the preparation.

Apart from being indicative for a low degree of presumably oxidative Ig alteration, a colourless or only slightly coloured preparation is visually much more appealing than a yellow or a yellow-brownish one.

A particularly high stability of the Ig preparation of the present invention can be achieved if the concentration of oxygen dissolved at room temperature is less than 175 μmol/l, preferably less than 150 μmol/l, more preferably less than 125 μmol/l, and most preferably less than 100 μmol/l.

Since for conventional Ig preparations, the effect of yellowish coloration is particularly pronounced for preparations having a high Ig concentration, the present invention particularly refers to a preparation comprising Ig in a mass-volume percentage of at least 5%, preferably at least 10%, more preferably at least 12%, more preferably at least 14%, more preferably at least 16%, more preferably at least 18%, and most preferably at least 20%. Preferably, the Ig preparation is a polyclonal Ig preparation, more preferably a polyclonal IgG preparation.

Compliance of the Ig preparation with the respective coloration requirements of the European Pharmacopoeia can be determined by the respective method given therein (Ph. Eur. 5.5, 2006, General methods 2.2.2 Degree of Coloration of Liquids).

Alternatively, compliance with the coloration requirements can also be determined by a spectrophotometric method, the results of which have been found to correlate with the results of the method according to the European Pharmacopoeia. Specifically, it has been found that an Ig preparation having a mean optical density $A_{350-500nm}$ (i.e. absorbance at 350 nm minus absorbance at the reference wavelength 500 nm) of less than 0.355 fully complies with the respective requirements of the European Pharmacopoeia.

When stored over 24 months at 25° C. in the dark, a mean increase of the optical density (absorbance) $A_{350-500nm}$ of only about 0.1 can be achieved according to the present invention, when stored over 36 months at 25° C. in the dark, a mean increase of the optical density of only about 0.15 can be achieved (corresponding to an approximate monthly increase of the absorbance of 0.004). When stored over 3 months at 5° C. under light exposure, a mean increase of the optical density $A_{350-500nm}$ of only about 0.04 can be achieved according to the present invention (corresponding to an approximate monthly increase of the absorbance of 0.01), which is in clear contrast to the mean increase for an Ig preparation in which the oxygen concentration is not reduced according to the present invention, said increase being about 1.2 (corresponding to an approximate monthly increase of the absorbance of 0.40). Further, when stored over 6 months at 37° C. in the dark, a mean increase of the optical density $A_{350-500nm}$ of only about 0.18 can be achieved according to the present invention (corresponding to an approximate monthly increase of the absorbance of 0.03), which is in clear contrast to the mean increase for an Ig preparation in which the oxygen concentration is not reduced according to the present invention, said increase being about 0.24 (corresponding to an approximate monthly increase of the absorbance of 0.04).

The Ig preparations of the present invention can be used both for the intravenous and the subcutaneous administration to a patient, by way of a non-limiting example for the treatment of PID or CVID. The use for the subcutaneous administration is however preferred.

Given the high concentration of Ig, the present invention allows smaller volumes of the preparation to be administered to the patient while maintaining the efficacy compared to conventionally available preparations having a lower Ig concentration.

Since the Ig preparation according to the present invention is preferably used for the subcutaneous administration to a human, the present invention also relates to the use of the Ig preparation for the preparation of a medicament for subcutaneous administration to a human. As for example reported by S. Misbah et al, Clinical and Experimental Immunology, 158 (Suppl. 1); pp. 51-59, there are various advantages of the subcutaneous administration of the preparation over the intravenous administration. In particular, venous access is not required and the need for premedication with corticosteroids and anti-histamines is reduced.

Also, when using the subcutaneous administration route the marked peaks typically seen with monthly IVIg infusions are dampened and persistently elevated Ig levels are obtained leading to a reduction in systemic side effects.

Preferably, the Ig comprised in the Ig preparation of the present invention essentially consists of IgG, but is in no way limited thereto. According to other preferred embodiments of the preparation of the present invention, the Ig comprises or essentially consists of IgM or comprises or essentially consists of IgA, respectively.

According to another aspect, the present invention further relates to a storage system for an Ig preparation, preferably a polyclonal Ig preparation, said storage system comprising a container having an interior, a first portion of said interior being occupied by the Ig preparation and the remaining second portion of said interior forming a headspace and being occupied by a gas, wherein in the gas of the headspace the content of oxygen is less than 20 vol-%. In the context of the present invention, the term "vol-%" has the meaning commonly used in the technical field and denotes the volume ratio of the respective gas component in relation to the total volume of the gas in which it is contained.

The gas in the headspace of the storage system of the present invention thus has a reduced oxygen content compared to the surrounding air. If stored in such a storage system, the oxygen dissolved in the Ig preparation can thus be kept at a concentration below 200 μmol/l, preferably below 175 μmol/l, more preferably below 150 μmol/l, even more preferably below 125 μmol/l, and most preferably below 100 μmol/l over a prolonged storage period, and yellowish coloration can be vastly reduced even if the Ig preparation is stored under light and at room temperature.

Methods for determining the oxygen content in the gas of the headspace are known to a skilled person. For example, the oxygen content can be determined by laser absorption spectroscopy, in particular tuneable diode laser absorption spectroscopy, thus eliminating interference of other components contained in the headspace gas. Specifically, the oxygen content can be determined by means of a device of the type LaserGas™ II (LaserGas Oy, Finland), whereby the absorption line of oxygen is scanned by means of a single-mode diode. The absorption of light by the oxygen molecules is measured by a detector, based on which the oxygen content of the headspace gas can be calculated.

It is preferred that in the gas of the headspace the content of oxygen is less than 16 vol-%, preferably less than 12 vol-%, more preferably less than 10 vol-%, and most preferably less than 7 vol-%. An oxygen content of less than 7 vol-% has been found to be particularly preferred, since Ig preparations stored under a respective headspace in the container has been shown to fully comply with the requirements of the European Pharmacopoeia even after a prolonged storage period of 24 months or longer, even after a storage period of 36 months or longer, even when stored at 25° C. (in the dark), as will be shown in detail below.

According to a very straightforward and thus preferred embodiment, the gas of the headspace is at least approximately at atmospheric pressure.

It is further preferred that in the gas of the headspace the content of inert gas is more than 80 vol-%, preferably more than 84 vol-%, more preferably more than 88 vol-%, more preferably more than 90 vol-%, and most preferably more than 93 vol-%. The inert gas may be e.g. nitrogen, argon, other noble gases or mixtures thereof. Given its availability, nitrogen is preferably used.

It is further preferred that the container of the gas-tight storage system comprises a vial, in particular a vial as standardized by DIN/ISO 8362-1.

According to a further preferred embodiment, the volume ratio of the headspace to the Ig preparation ranges from about 0.1:1 to 0.9:1, depending on the vial used. For a 6R vial, for example, the ratio is typically about 0.9:1 whereas for a 20R vial, the ratio is typically at about 0.1:1.

In particular, the storage system of the invention improves the stability of an Ig preparation after a prolonged storage period of 24 months, even of 36 months, at room temperature in the dark. When using a 20% Ig preparation as reference, the storage system of the invention provides that the absorbance $A_{350\text{-}500nm}$ of the immunoglobulin preparation remains below 0.28 upon storage for 24 months at 25° C. in the dark, preferably the absorbance $A_{350\text{-}500nm}$ remains below 0.355 when measured for a 20% Ig preparation after storage for 6 months at 37° C. in the dark. The storage system of the invention provides a stable immunoglobulin preparation showing an increase in $A_{350\text{-}500nm}$ of less than 0.18, preferably of less than 0.17, even more preferably of less than 0.16, when stored at 25° C. in the dark for 36 months. The storage system of the invention provides a stable immunoglobulin preparation showing an increase in $A_{350\text{-}500nm}$ of less than 0.22, preferably of less than 0.20, even more preferably of less than 0.19, when stored at 37° C. in the dark for 6 months.

According to a further aspect, the present invention also relates to a process for providing a storage system for an Ig preparation comprising the steps that the Ig preparation is filled into a container and the container is sealed, wherein prior to the sealing the headspace of the container is filled with a gas such that the oxygen content in the gas of the headspace is less than 20 vol-%, preferably less than 16 vol-%, more preferably less than 12 vol-%, even more preferably less than 10 vol-%, and most preferably less than 7 vol-%. This "inert gassing" of the headspace allows the concentration of the oxygen dissolved to be kept at a concentration below 200 μmol/l preferably below 175 μmol/l, more preferably below 150 μmol/l, even more preferably below 125 μmol/l, and most preferably below 100 μmol/l over a prolonged storage period. Preferably, the prolonged storage period is longer than 24 months, preferably even longer than 36 months, at 25° C. (or room temperature) in the dark. In particular, the process of the invention improves the stability of an Ig preparation after a prolonged storage period of 24 months, even of 36 months, at room temperature in the dark. When using a 20% Ig preparation as reference, the process of the invention provides that the absorbance $A_{350\text{-}500nm}$ of the immunoglobulin preparation remains below 0.28 upon storage for 24 months at 25° C. in the dark, preferably the absorbance $A_{350\text{-}500nm}$ remains below 0.355 when measured for a 20% Ig preparation after storage for 6 months at 37° C. in the dark. The process of the invention provides a stable immunoglobulin preparation showing an increase in $A_{350\text{-}500nm}$ of less than 0.18, preferably of less than 0.17, even more preferably of less than 0.16, when stored at 25° C. in the dark for 36 months. The process of the invention provides a stable immunoglobulin preparation showing an increase in $A_{350\text{-}500nm}$ of less than 0.22, preferably of less than 0.20, even more preferably of less than 0.19, when stored at 37° C. in the dark for 6 months.

Preferably, the gas of the headspace of the storage system obtained is at atmospheric pressure.

Alternatively or additionally to the above process, an Ig preparation defined above with a reduced concentration of oxygen dissolved can be obtained by subjecting the Ig preparation or its solvent to a degassing step and/or a gassing step using an inert gas. It is thereby preferred that the solvent of the Ig preparation, typically water, is subjected to the degassing and/or gassing step prior to the formulation of the Ig preparation. Degassing can for example be obtained by storing the solvent at an elevated temperature or at a reduced pressure. Gassing using an inert gas can for example be performed by introducing the inert gas into the respective preparation or its solvent.

In accordance with the above, the present invention relates according to a further aspect also to the use of a gas having an oxygen content of less than 20 vol-% for increasing the storage stability of an immunoglobulin preparation comprising immunoglobulin in a mass-volume percentage of at least 4%. As given above, the gas is thereby preferably used in the headspace of a container in which the Ig preparation is stored.

With the storage system of the invention, or the process of the invention, or the use of a gas with an oxygen content of less than 20% according to the invention, a reduction in the mean increase of absorbance at 350 nm for an Ig preparation of at least 10% is achievable, preferably of more than 12%, 14%, 16%, 18% or 20%, more preferably of more than 25%, 30%, 35%, 38%, 40%, or even 45% can be achieved when stored for a prolonged period in the dark. With the storage system or process of the invention, this can be achieved for preparations comprising Ig in a mass-volume percentage of at least 5%, preferably at least 10%, more preferably at least 12%, more preferably at least 14%, more preferably at least 16%, more preferably at least 18%, and most preferably at least 20%.

A detailed description of a process according to the present invention is given in the example below.

EXAMPLES

Ig Preparation

The technical effect achieved by the present invention was assessed using IgPro20.

IgPro20 is a ready-to-use, 20% (200 g/l) liquid preparation of polyvalent human IgG for subcutaneous administration, manufactured from large pools of human plasma. Its protein moiety is ≥98% IgG, of which over 90% is in the form of monomers+ dimers. IgPro20 is formulated with the stabilizer L-proline (250 mmol/L) at pH 4.8 without preservatives.

Filling of the Ig Preparation

During aseptic filling of IgPro20 into a vial, the headspace of the vial was gassed with nitrogen.

Specifically, gassing with nitrogen was carried out in two steps:

a) directly after introducing the Ig preparation into the vial, sterile-filtered nitrogen gas was filled into the headspace by means of an inflation needle extending into the headspace;

b) during insertion of the plug for sealing the vial, nitrogen gas was blown onto the opening of the vial by a further inflation needle extending in angular direction with regard to the axis of the opening.

The nitrogen gas used was sterile-filtered using a sterile filter of the type KAO2PFRP8 of Pall Corporation. The operating pressure of the gassing equipment was set to about 0.5 bar.

By the above procedure, a storage system can be provided having a headspace which immediately after sealing of the vial has an oxygen content of less than 4.5 vol-%. Given the fact that the preparation is not degassed or gassed with an inert gas before filling into the vial, the oxygen content in the gas of the headspace might increase until an equilibrium between the immunoglobulin and the gas is established. Even in this case, the content of oxygen remains below 7 vol-%.

Storage Conditions

Figure 3:
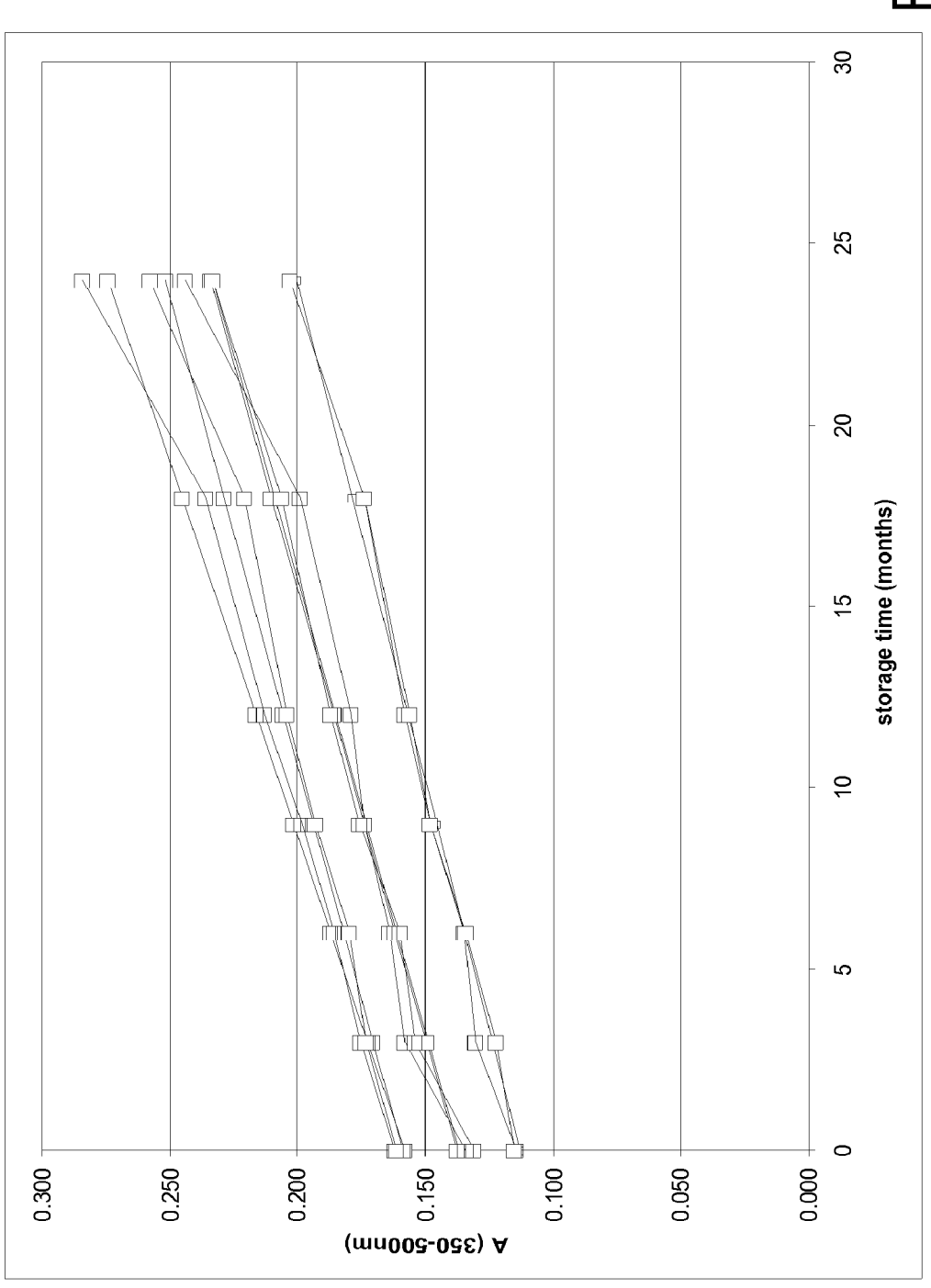

The storage conditions and test intervals of the long-term stability program for IgPro20 were chosen according to the International Conference on Harmonization (ICH) of Technical Requirements for Registration of Pharmaceuticals for Human Use guideline Q1A(R2). Long-term storage for up to 24 months at 25° C. is shown in FIG. 3 below.

In order to simulate secondary packaging, the vials were stored at a temperature of 37° C. in the dark.

A horizontal position of the container maintained contact of the solution with the stopper, in accordance with ICH guideline Q5C.

Quantification of Yellowish Coloration

Figure 2:
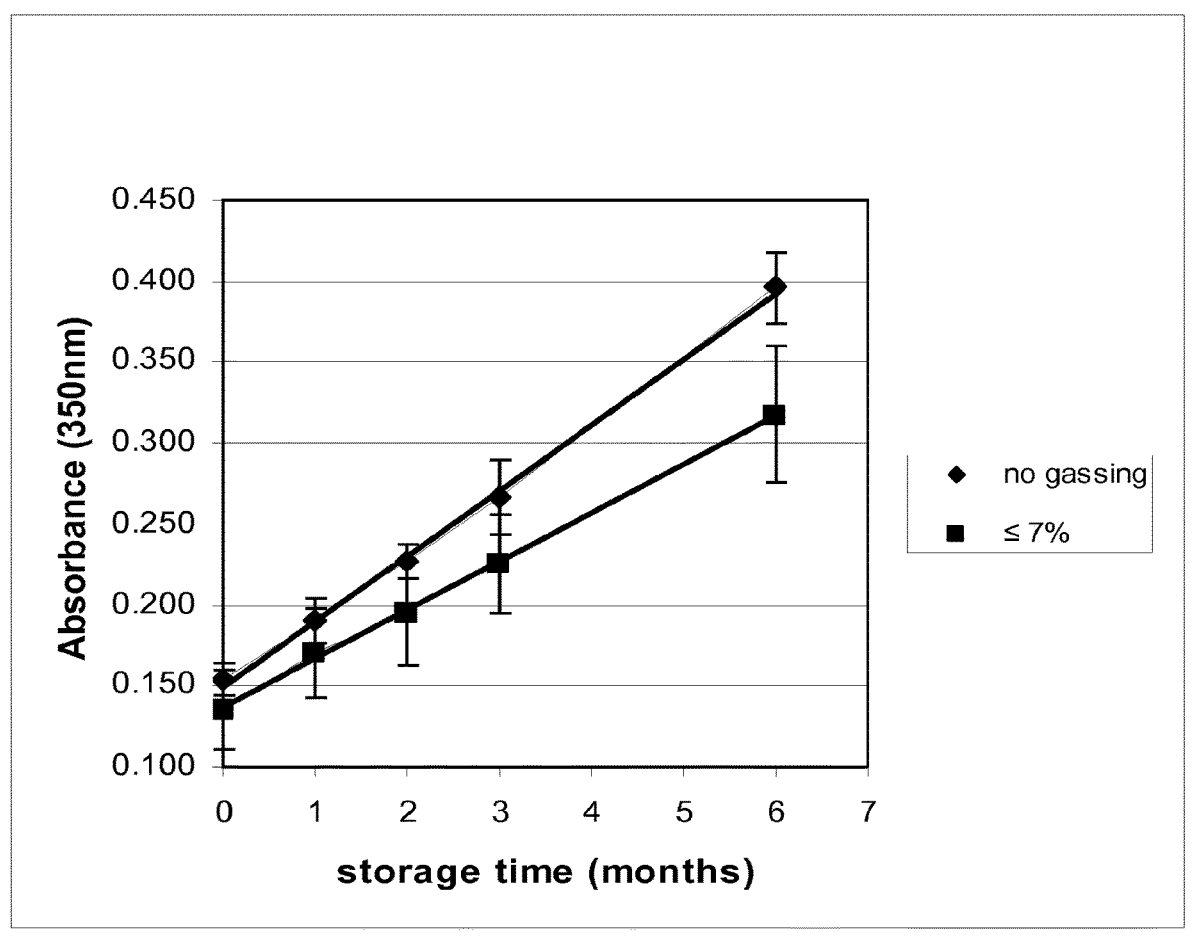

In order to quantify yellowing of the Ig preparation, its mean optical density at 350 to 500 nm has been determined without inert gassing of the headspace (diamonds), using a gas in the headspace having an oxygen content of 16 vol-% (squares), 12 vol-% (triangles), 10 vol-% (crosses), 7 vol-% (stars) and less than 7 vol-% (circles), respectively; and FIG. 2 is a graphical representation of the optical density (absorbance) $A_{350\text{-}500nm}$ of the Ig preparation stored as a function of storage time after storage at 37° C. in the dark without inert gassing of the headspace (diamonds) and using a gas in the headspace having an oxygen content of at most 7 vol-% (squares), respectively, and FIG. 3 is a graphical representation of the mean optical density (absorbance) $A_{350\text{-}500nm}$ of a number of samples of the Ig preparation as a function of storage time when stored at 25° C. in the dark using a gas in the headspace having an oxygen content of less than 7 vol-%.

As can be seen from FIG. 1, yellowing of the immunoglobulin preparation over time is reduced by using a gas having a reduced oxygen content (and thus also a reduced oxygen partial pressure) in the headspace. Specifically, by using a gas having an oxygen content of less than 7 vol-%, the optical density $A_{350\text{-}500nm}$ is less than 0.35 even after storage for 6 months, thus fully complying with the requirements of the European Pharmacopoeia after prolonged storage. The concentration of oxygen dissolved in the respective sample at room temperature is less than 100 µmol/l.

Referring to FIG. 2, a mean increase of the optical density $A_{350\text{-}500nm}$ of only about 0.18 can be achieved according to the present invention when stored over 6 months at 37° C. in the dark using a gas in the headspace having an oxygen content of at most 7 vol-%. This is in clear contrast to the mean increase for an Ig preparation stored without gassing of the headspace, said increase being about 0.24.

As shown in FIG. 3, a mean increase of the mean optical density $A_{350\text{-}500nm}$ of only about 0.1 can be achieved according to the present invention when stored over 24 months at 25° C. in the dark.

As shown in Table 1 below, the mean optical density is still below 0.355 even after storage over 36 months at 25° C. in the dark, and even lower if stored at 5° C. in the dark. The values of 6 different lots are shown.

TABLE 1

| | 25° C. | | | | | | 5° C. | | | | | |
| --- | --- | --- | --- | --- | --- | --- | --- | --- | --- | --- | --- | --- |
| | 30 months | | | 36 months | | | 30 months | | | 36 months | | |
| | $O_2$ µmol/L | % $O_2$ | $A_{350}$ | $O_2$ µmol/L | % $O_2$ | $A_{350}$ | $O_2$ µmol/L | % $O_2$ | $A_{350}$ | $O_2$ µmol/L | % $O_2$ | $A_{350}$ |
| | 79.2 | 6.3 | 0.270 | 83.5 | 6.6 | 0.319 | 61.3 | 4.8 | 0.156 | 58.4 | 4.6 | 0.158 |
| | 75.8 | 6.0 | 0.229 | 79.9 | 6.3 | 0.249 | 56.0 | 4.4 | 0.132 | 54.8 | 4.3 | 0.130 |
| | 82.4 | 6.5 | 0.297 | 86.3 | 6.8 | 0.332 | 65.3 | 5.1 | 0.181 | 62.4 | 4.9 | 0.186 |
| | 53.3 | 4.2 | 0.298 | 54.3 | 4.3 | 0.289 | 66.0 | 5.2 | 0.155 | 62.3 | 4.9 | 0.159 |
| | 55.7 | 4.4 | 0.231 | 57.3 | 4.5 | 0.244 | 62.3 | 4.9 | 0.133 | 58.5 | 4.6 | 0.131 |
| | 54.7 | 4.3 | 0.290 | 56.3 | 4.4 | 0.318 | 63.5 | 5.0 | 0.180 | 59.8 | 4.7 | 0.179 | after several intervals of storing. This is based on the finding that the mean optical density can be correlated to the standardized examination of the coloration of liquids as described in the European Pharmacopoeia (Ph. Eur. 5.6, January 2005, General methods 2.2.2, Degree of Coloration of Liquids).

The technical effect achieved by the present invention is illustrated by way of the attached figures, of which FIG. 1 is a graphical representation of the optical density (absorbance) $A_{350\text{-}500nm}$ of the Ig preparation stored as a function of storage time after storage at 5° C. under light Table 2 shows the mean monthly increase in absorbance $A_{350\text{-}500nm}$ in different storage conditions. For all conditions tested, keeping the oxygen concentration below 100 µmol/l, or below 7% oxygen in the headspace, leads to significantly lower increase in absorbance, indicating significantly higher stability of the IgG preparation. All samples were stored in the dark. Data were collected for 24 or 36 months: during this time, the increase of absorbance over time was about linear.

TABLE 2

| Storage temperature | Oxygen in headspace | Mean monthly increase in $A_{350\text{-}500\ nm}$ | $A_{350\text{-}500\ nm}$ reduction by O2 reduction |
|---|---|---|---|
| 37° C. | <7% | 0.030 | 42.5% |
|  | 20% (air) | 0.052 |  |
| 25° C. | <7% | 0.0042 | 19.9% |
|  | 20% (air) | 0.0052 |  |
| 5° C. | <7% | 0.00037 | 47.8% |
|  | 20% (air) | 0.00071 |  |

The invention claimed is:

1. A storage system for a ready-to-use liquid immuno-globulin preparation for intravenous or subcutaneous administration comprising a container having an interior, a first portion of said interior being occupied by the ready-to-use liquid immunoglobulin preparation, wherein the ready-to-use liquid immunoglobulin preparation comprises immunoglobulin in a mass-volume percentage of at least 4%, wherein the concentration of oxygen dissolved in the preparation at room temperature is less than 150 μmol/l, wherein the absorbance at 350 nm minus the absorbance at 500 nm (absorbance $A_{350\text{-}500nm}$) of the immunoglobulin preparation remains below 0.28 upon storage for 24 months at 25° C. in the dark, and the remaining portion of said interior forming a headspace and being occupied by a gas other than air, wherein the content of oxygen in the gas of the headspace remains less than 20 vol-% during said storage.

2. The storage system according to claim 1, wherein the immunoglobulin preparation comprises immunoglobulin in a mass-volume percentage of at least 10%.

3. The storage system according to claim 1, wherein the immunoglobulin preparation comprises immunoglobulin in a mass-volume percentage of 14-20%.

4. The storage system according to claim 1, wherein the immunoglobulin preparation comprises immunoglobulin in a mass-volume percentage of at least 18%.

5. The storage system according to claim 1, wherein the immunoglobulin preparation comprises immunoglobulin in a mass-volume percentage of at least 20%.

6. The storage system according to claim 1, wherein the preparation has a mean increase in absorbance A350-500 nm of less than 0.2 upon storage of 6 months at 37° C. in the dark.

7. The storage system according to claim 1, wherein the immunoglobulin comprised in the immunoglobulin preparation consists essentially of IgG.

8. The storage system according to claim 1, wherein the absorbance at 350 nm minus the absorbance at 500 nm (absorbance A350-500 nm) of the immunoglobulin preparation remains below 0.28 upon storage for 36 months at 25° C. in the dark.

9. The storage system according to claim 1, wherein the concentration of oxygen dissolved in the preparation at room temperature is less than 125 μmol/l.

10. The storage system according to claim 9, wherein the immunoglobulin preparation comprises immunoglobulin in a mass-volume percentage of at least 10%.

11. The storage system according to claim 9, wherein the immunoglobulin preparation comprises immunoglobulin in a mass-volume percentage of 14-20%.

12. The storage system according to claim 9, wherein the absorbance at 350 nm minus the absorbance at 500 nm (absorbance A350-500 nm) of the immunoglobulin preparation remains below 0.28 upon storage for 36 months at 25° C. in the dark.

13. The storage system according to claim 1, wherein the concentration of oxygen dissolved in the preparation at room temperature is less than 100 μmol/l.

14. The storage system according to claim 13, wherein the immunoglobulin preparation comprises immunoglobulin in a mass-volume percentage of at least 10%.

15. The storage system according to claim 13, wherein the immunoglobulin preparation comprises immunoglobulin in a mass-volume percentage of 14-20%.

16. The storage system according to claim 13, wherein the absorbance at 350 nm minus the absorbance at 500 nm (absorbance A350-500 nm) of the immunoglobulin preparation remains below 0.28 upon storage for 36 months at 25° C. in the dark.

17. The storage system of claim 1, wherein the immunoglobulin is a polyvalent human IgG derived from a pool of human plasma.

18. The storage system of claim 3, wherein the immunoglobulin is a polyvalent human IgG derived from a pool of human plasma.

19. The storage system of claim 5, wherein the immunoglobulin is a polyvalent human IgG derived from a pool of human plasma.

20. The storage system of claim 15, wherein the immunoglobulin is a polyvalent human IgG derived from a pool of human plasma.

* * * * *